United States Patent
Jones

(10) Patent No.: US 9,238,106 B2
(45) Date of Patent: Jan. 19, 2016

(54) DOSE SETTING MECHANISM FOR PRIMING A DRUG DELIVERY DEVICE

(75) Inventor: Christopher John Jones, Broadway (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 1405 days.

(21) Appl. No.: 12/788,728

(22) Filed: May 27, 2010

(65) Prior Publication Data

US 2010/0331789 A1 Dec. 30, 2010

Related U.S. Application Data

(60) Provisional application No. 61/182,841, filed on Jun. 1, 2009.

(30) Foreign Application Priority Data

Jul. 10, 2009 (EP) ..................................... 09009048

(51) Int. Cl.
*A61M 5/31* (2006.01)
*A61M 5/24* (2006.01)
*A61M 5/315* (2006.01)

(52) U.S. Cl.
CPC ............... *A61M 5/24* (2013.01); *A61M 5/3146* (2013.01); *A61M 5/31511* (2013.01); *A61M 5/31535* (2013.01); *A61M 5/31551* (2013.01); *A61M 5/31561* (2013.01); *A61M 5/31585* (2013.01); *A61M 2005/2407* (2013.01); *A61M 2005/2488* (2013.01); *A61M 2005/2492* (2013.01); *A61M 2005/3104* (2013.01); *A61M 2005/3125* (2013.01)

(58) Field of Classification Search
CPC ............... A61M 2005/2073; A61M 2005/202; A61M 2005/1402; A61M 5/3146; A61M 5/24
See application file for complete search history.

(56) References Cited

U.S. PATENT DOCUMENTS

| | | |
|---|---|---|
| 3,302,462 A | 2/1967 | Pursell |
| 5,423,752 A | 6/1995 | Haber et al. |
| 5,514,097 A | 5/1996 | Knauer |
| 5,584,815 A | 12/1996 | Pawelka et al. |
| 5,591,136 A | 1/1997 | Gabriel |
| 5,792,117 A | 8/1998 | Brown |
| 5,820,602 A | 10/1998 | Kovelman et al. |
| 6,090,080 A | 7/2000 | Jost et al. |
| 6,936,032 B1 | 8/2005 | Bush, Jr. et al. |

(Continued)

FOREIGN PATENT DOCUMENTS

| | | |
|---|---|---|
| DE | 93 01 334 U1 | 4/1993 |
| DE | 197 30 999 C1 | 12/1998 |

(Continued)

OTHER PUBLICATIONS

Machine Deisgn, Penton Media, vol. 65, No. 11 (1993) p. 36 "Standard Compression Springs Save Space".

*Primary Examiner* — Nathan R Price
*Assistant Examiner* — Anh Bui
(74) *Attorney, Agent, or Firm* — McDonnell Boehnen Hulbert & Berghoff LLP

(57) ABSTRACT

A method and system for priming a drug delivery device. The drug delivery device includes a forced priming feature that requires the user to move the dose dial sleeve axially to cause the spindle to pre-load a cartridge bung before a first dose can be dialed.

14 Claims, 2 Drawing Sheets

(56) References Cited

U.S. PATENT DOCUMENTS

| | | |
|---|---|---|
| 2004/0127858 A1* | 7/2004 | Bendek et al. ............... 604/208 |
| 2004/0162528 A1 | 8/2004 | Horvath et al. |
| 2004/0186437 A1 | 9/2004 | Frenette et al. |
| 2004/0210199 A1 | 10/2004 | Atterbury et al. |
| 2004/0236285 A1 | 11/2004 | Fisher et al. |
| 2005/0137571 A1 | 6/2005 | Hommann |
| 2005/0261634 A1* | 11/2005 | Karlsson ...................... 604/197 |
| 2006/0153693 A1 | 7/2006 | Fiechter et al. |
| 2006/0258988 A1 | 11/2006 | Keitel et al. |
| 2006/0270985 A1* | 11/2006 | Hommann et al. .......... 604/136 |
| 2007/0016142 A1* | 1/2007 | Burren et al. ................ 604/207 |
| 2007/0021718 A1 | 1/2007 | Burren et al. |
| 2008/0015511 A1* | 1/2008 | Veasey et al. ............... 604/187 |
| 2008/0027397 A1 | 1/2008 | DeRuntz et al. |
| 2008/0077095 A1 | 3/2008 | Kirchhofer |
| 2008/0208123 A1 | 8/2008 | Hommann |
| 2009/0227959 A1 | 9/2009 | Hirschel et al. |

FOREIGN PATENT DOCUMENTS

| | | |
|---|---|---|
| DE | 298 18 721 U1 | 3/2000 |
| DE | 10 2005 063 311 A1 | 8/2006 |
| DE | 10 2005 060 928 A1 | 6/2007 |
| DE | 10 2006 038 123 A1 | 2/2008 |
| DE | 10 2007 026 083 A1 | 11/2008 |
| EP | 0 897 728 A1 | 2/1999 |
| EP | 0 937 471 A2 | 8/1999 |
| EP | 0 937 472 A2 | 8/1999 |
| EP | 1 541 185 A1 | 6/2005 |
| EP | 1 776 975 A2 | 4/2007 |
| EP | 1 923 084 A1 | 5/2008 |
| GB | 2 443 390 A | 5/2008 |
| WO | 92/18180 A1 | 10/1992 |
| WO | 93/07922 A1 | 4/1993 |
| WO | 96/23973 A1 | 8/1996 |
| WO | 96/39214 A1 | 12/1996 |
| WO | 97/10864 A1 | 3/1997 |
| WO | 99/03520 A1 | 1/1999 |
| WO | 01/19434 A1 | 3/2001 |
| WO | 03/080160 A1 | 10/2003 |
| WO | 2004/020028 A1 | 3/2004 |
| WO | 2004/064902 A1 | 8/2004 |
| WO | 2004/078241 A1 | 9/2004 |
| WO | 2004/078242 A2 | 9/2004 |
| WO | 2004/078293 A1 | 9/2004 |
| WO | 2005/018721 A1 | 3/2005 |
| WO | 2005/021072 A1 | 3/2005 |
| WO | 2005/044346 A2 | 5/2005 |
| WO | 2005/123159 A2 | 12/2005 |
| WO | 2006/024461 A1 | 3/2006 |
| WO | 2006/058883 A2 | 6/2006 |
| WO | 2006/079481 A1 | 8/2006 |
| WO | 2006/089767 A1 | 8/2006 |
| WO | 2006/114395 A1 | 11/2006 |
| WO | 2006/125328 A1 | 11/2006 |
| WO | 2007/017052 A1 | 2/2007 |
| WO | 2007/067889 A1 | 6/2007 |
| WO | 2008/031235 A1 | 3/2008 |
| WO | 2008/074897 A1 | 6/2008 |
| WO | 2008/116766 A1 | 10/2008 |
| WO | 2008/128373 A1 | 10/2008 |

* cited by examiner

DOSE SETTING MECHANISM FOR PRIMING A DRUG DELIVERY DEVICE

BACKGROUND

1. Field of the Present Patent Application

The present patent application is generally directed to drug delivery devices. More particularly, the present patent application is generally directed to drug delivery devices, such as pen type drug delivery devices. Such devices provide for self administration of medicinal product from a multi-dose cartridge and permit a user to set the delivery dose. The present application may find application in both resettable (i.e., reusable) and non-resettable (i.e., non-reusable) type drug delivery devices. However, aspects of the invention may be equally applicable in other scenarios as well. Specifically, my invention is directed to a mechanism and method to require a user to prime the drug delivery device before the first injection.

2. Background

Pen type drug delivery devices have application where regular injection by persons without formal medical training occurs. This is increasingly common among patients having diabetes where self-treatment enables such patients to conduct effective management of their disease.

In certain types of medication delivery devices, such as pen type devices, cartridges of medication are used. These cartridges are housed in a cartridge holder or cartridge housing. Such cartridges include a bung or stopper at one end. At the other end of the cartridge, the cartridge comprises a pierceable seal. To dispense a dose of medication from such a cartridge, the medication delivery device has a dose setting mechanism that uses a spindle to move in a distal direction towards the cartridge and to press a distal end of the spindle against the bung. This expels a certain set dose of medication from the cartridge. In order to insure dose accuracy, it is important that the distal end of the spindle remain on the bung of the cartridge before, during and after injection of a dose of medicament.

One perceived disadvantage of certain know medication delivery devices is that because of the various tolerance differences that may occur during manufacturing (e.g., tolerance differences that may arise during component molding) of the various parts making up the drug delivery device and the desire to not pre-load the bung axially in the assembled device, there may be a gap between the end of the spindle and the cartridge bung when the medication delivery device is assembled. In other words, when initially assembled, the cartridge (and hence cartridge bung) may not be in contact with the distal end of the spindle. Therefore, if a user using the drug delivery device for the first time dials a dose, the actual dose received may be equal to the dialed dose less the initial gap between the distal end of the spindle and cartridge bung. The air gap between the cartridge bung and distal end of the spindle may be equivalent to a dose that causes the received dose that is outside preferred dose accuracy limits. For example, this air gap may be equivalent to the loss of between 0 and 10 units (i.e., 0-0.14 milliliters) of drug product on the first dose.

There is, therefore, a general need to take these perceived issues into consideration when designing either resettable or non-resettable drug delivery devices, such as pen type drug delivery devices. My invention solves the above-described problem by requiring the user to prime the injection device to close the gap by pre-loading the bung.

SUMMARY

According to an exemplary arrangement, a dose setting mechanism for a drug delivery device is provided. The drug delivery device includes a dose dial sleeve and an inner body. The dose dial sleeve is coupled to a nut that is rotationally engaged to the inner body. In this exemplary arrangement, the dose dial sleeve moves axially in the distal direction during priming of the drug delivery device relative to the nut to form an irreversible lock. Further, the dose dial sleeve rotates on a helical path during dose setting of the drug delivery device.

According to another arrangement, my invention relates to a drug delivery device having a forced priming feature comprising a cartridge holder containing a cartridge of medicament sealed with a bung and a dose dialing assembly containing a spindle configured to move the bung in an axial direction during dose delivery. There is also an inner body having a rotational counter stop, a nut threaddedly engaged with the inner body and attached to a number sleeve having a proximal and a distal end. The number sleeve has a first and a second axial position relative to the nut. The distal end of number sleeve has a sliding lock that engages the nut when the number sleeve is in the second distal position. There is a stop on the proximal end of the number sleeve that abuts the rotational counter stop on the inner body when the number sleeve is in the first axial position to prevent a user from setting a dose of medicament.

My invention also is directed to a method of ensuring a user primes the drug delivery device before setting a first dose. One method involves providing to a user a dose dial sleeve coupled with a nut threaddedly engage on an inner body of a drug delivery device. The user is required to move the dose dial sleeve axially in the distal direction a specific distance to irreversibly engage the nut. This pre-loads the bung in the cartridge and thus primes the drug delivery device.

Yet another method involves providing a user with a drug delivery device having a cartridge holder portion and a dose dialing portion containing a spindle, where the cartridge holder contains a cartridge containing a bung and medicament. A number sleeve (i.e. dose dial sleeve) located in the dose dialing portion is in a first axial position. The user is prevented from dialing a dose by providing a rotational stop on the number sleeve such that it engages a counter stop on an inner body when the number sleeve is in the first axial position. The user is required to move the number sleeve from the first axial position to a second axial position to disengage the stop and counter stop and to engage a sliding lock between the number sleeve and a nut attached to the inner body.

My invention also relates to a drug delivery device having a forced priming feature where the device has a cartridge holder containing a cartridge of medicament sealed with a bung and a dose dialing assembly containing a spindle configured to move the bung in an axial direction during dose delivery. The device also has an inner body with a rotational counter stop. It has a nut threaddedly engaged with the inner body and is in rotational engagement to a number sleeve having proximal and distal ends and having first and second axial positions. The inner body has a collar axially retained but rotationally free that is threaddedly engaged with the distal end of the number sleeve such that rotation of the collar causes the number sleeve to move from the first axial position, where a user is prevented from setting a dose, to the second axial position where a dose can then be set. Movement from the first position to the second position causes the spindle to move axially preloading the bung thus priming the injection device.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which.

DETAILED DESCRIPTION

Figure 1:
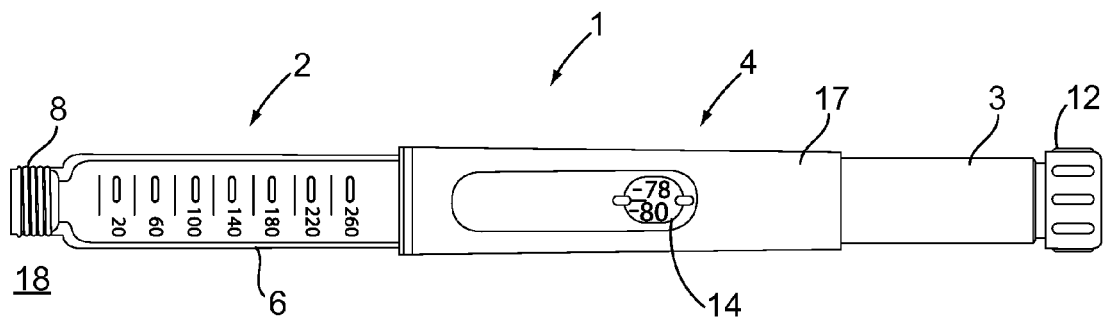
FIG. 1 illustrates the drug delivery device in accordance with the one aspect of the present invention with a cap removed and showing a cartridge holder.

Referring to FIG. 1, there is shown a drug delivery device 1 in accordance with an exemplary arrangement. The drug delivery device 1 comprises a housing having a first cartridge retaining part 2, and a dose setting mechanism 4. The drug delivery device may be a resettable drug delivery device (i.e., a reusable device) or alternatively a non-resettable drug delivery device (i.e., a non-reusable device). A first end of the cartridge retaining part 2 and a second end of the dose setting mechanism 4 are secured together by connecting features. For non-resettable devices, these connecting features would be permanent and non-reversible. For resettable devices, these connecting features would be releasable.

In this illustrated arrangement, the cartridge housing 2 is secured within the second end of the dose setting mechanism 4. A removable cap (not shown) is releasably retained over a second end or distal end of a cartridge retaining part or cartridge housing. The dose setting mechanism 4 comprises a dose dial grip 12 and a window or lens 14. A dose scale arrangement is viewable through the window or lens 14. To set a dose of medication contained within the drug delivery device 1, a user rotates the dose dial grip 12 such that a dialed dose will become viewable in the window or lens 14 by way of the dose scale arrangement.

FIG. 1 illustrates the medical delivery device 1 with the cover cap removed from a distal end 18 of the medical delivery device 1. This removal exposes the cartridge housing 6. Preferably, a cartridge (not shown) from which a number of doses of a medicinal product may be dispensed, is provided in the cartridge housing 6. Preferably, the cartridge contains a type of medicament that can be administered relatively often, such as once or more times a day. One such medicament is either long acting or short acting insulin or an insulin analog. The cartridge comprises a bung or stopper that is retained near a second end or a proximal end of the cartridge. The medical delivery device also comprises a driver having a spindle (not illustrated in FIG. 1, but is illustrated as items 7 and 5 in FIGS. 3 and 5). As discussed above, before the device is primed, there may or may not be a gap between the end of the spindle and the cartridge bung.

The cartridge housing 6 has a distal end and a proximal end. Preferably, the distal end of the cartridge housing 6 comprises a hub 8 for attaching a removable needle assembly. However, other needle assembly connection mechanisms could also be used. If the drug delivery device 1 comprises a resettable device, the cartridge proximal end is removably connected to the dose setting mechanism 4. In one preferred embodiment, cartridge housing proximal end is removably connected to the dose setting mechanism 4 via a bayonet connection. However, as those of ordinary skill in the art will recognize, other types of removable connection methods such as threads, partial threads, ramps and detents, snap locks, snap fits, and luer locks may also be used.

As previously mentioned, the dose setting mechanism 4 of the drug delivery device illustrated in FIG. 1 may be utilized as a reusable drug delivery device. (i.e., a drug delivery device that can be reset) Where the drug delivery device 1 comprises a reusable drug delivery device, the cartridge is removable from the cartridge housing 6. The cartridge may be removed from the device 1 without destroying the device 1 by merely having the user disconnect the dose setting mechanism 4 from the cartridge housing 6.

In use, once the cap is removed, a user can attach a suitable needle assembly to the hub 8 provided at the distal end of the cartridge housing 6. Such needle assembly may be, for example, screwed onto a distal end of the housing 6 or alternatively may be snapped onto this distal end. After use, the replaceable cap may be used to re-cover the cartridge housing 6. Preferably, the outer dimensions of the replaceable cap are similar or identical to the outer dimensions of the dose setting mechanism 4 so as to provide an impression of a unitary whole when the replaceable cap is in position covering the cartridge housing 6 when the device is not in use.

Figure 2:
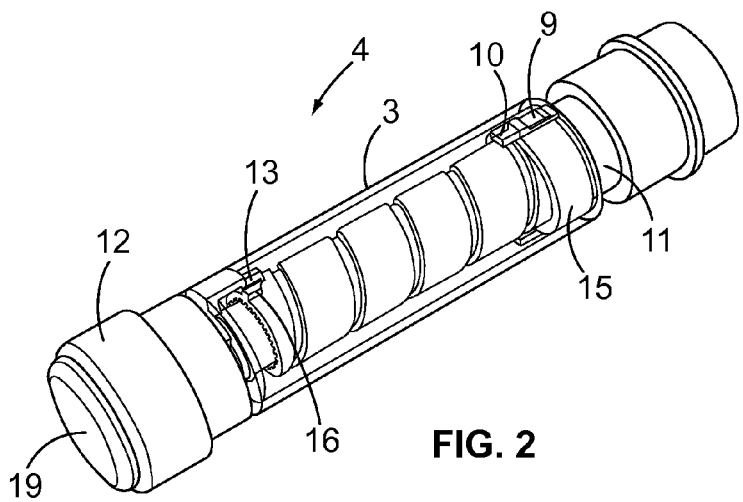
FIG. 2 is a perspective view of one embodiment of a dose setting mechanism in accordance with my invention for a drug delivery device such as the one shown in FIG. 1.
Figure 3:
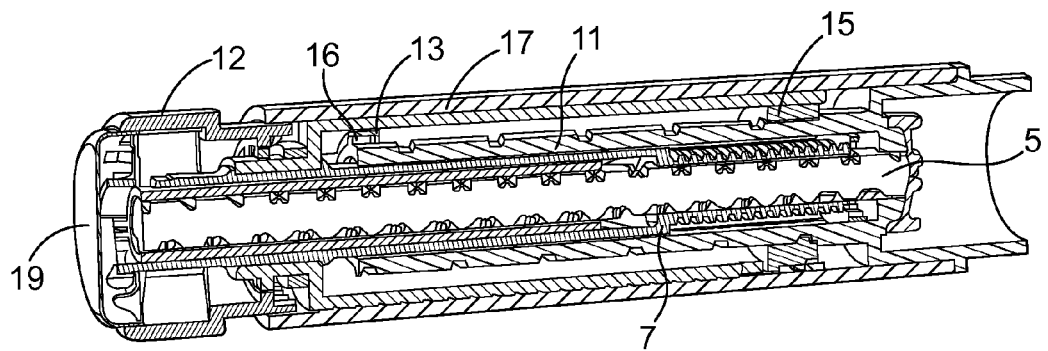
FIG. 3 illustrates a cut-away side view of the dose setting mechanism of FIG. 2.

FIGS. 2 and 3 illustrate perspective and cross sectional views of a first arrangement of a dose setting mechanism 4. Those of skill in the art will recognize that dose setting mechanism 4 may include a connection mechanism for releasably connecting to a cartridge holder, like the cartridge holder 6 illustrated in FIG. 1. However, as those of ordinary skill in the art will recognize, the dose setting mechanism may also include a permanent connection mechanism for permanently connecting to a cartridge holder.

With reference to FIGS. 2 and 3, the dose setting mechanism 4 comprises a dose dial grip 12, an outer housing 17, a driver 7, a dose dial sleeve 3, and an inner body 11. The dose dial sleeve 3 is coupled to a nut 15 that is rotationally engaged to the inner body 11. The nut has a permanent rotational engagement with the dial sleeve such that they cannot rotate relative to each other. FIGS. 2 and 3 show the dose setting mechanism in the non-primed configuration where a new cartridge of medicament has been loaded into the cartridge holder. In this position the dial (number) sleeve has a relatively small amount of axial clearance relative to the nut where the dial sleeve is set back proximally from the nut. This allows the number sleeve to axially travel inward relative to the nut such that an irreversible lock is formed between male and female parts 9 and 10. This irreversible lock prevents the dial sleeve from travelling rearward relative to the nut. In prefilled disposable injection devices the components are assembled and supplied to the user with the number sleeve in its rearward position relative to the nut. In reusable devices the dose setting mechanism is configured to allow the user to un-lock the irreversible lock as part of the procedure for removing an empty cartridge and inserting a new full cartridge. The important aspect is that the lock remains irreversible during dispensing of the medicament from the cartridge from the first dose to the last dose. In the non-primed first position of the dose dial sleeve, parts 9 and 10 are discouraged from engaging with each other by an interference fit between the two components. This can take the form of a detent or snap fit mechanism or other known male/female connection that requires a specific application of force to connect the two components. In other words, the friction between parts 9 and 10 may only be overcome by input from the user.

When the dial sleeve is in its first position as shown in FIGS. 2 and 3, i.e. axially displaced in the proximal direction away from the nut, the dial sleeve is prevented from "dialing out" in the dose setting direction by thread stop 13 and inner body stop 16. Likewise, the dial sleeve may also be prevented from "dialing in" by a stop 100 between the nut and the inner body. To release the dose setting mechanism from this initial non-primed position, the user is forced or required to push dose button 19 axially, which in turn causes the dial sleeve to move axially to force parts 9 and 10 together to engage or create the lock. This axially movement of the dial sleeve also causes driver 7 to act on spindle 5 moving it in the axial direction and thus pre-loads the cartridge bung. The injection device at this point is now primed. The dial sleeve is also released from the inner body stop 16 allowing it to be freely rotated during dose setting.

Figure 4:
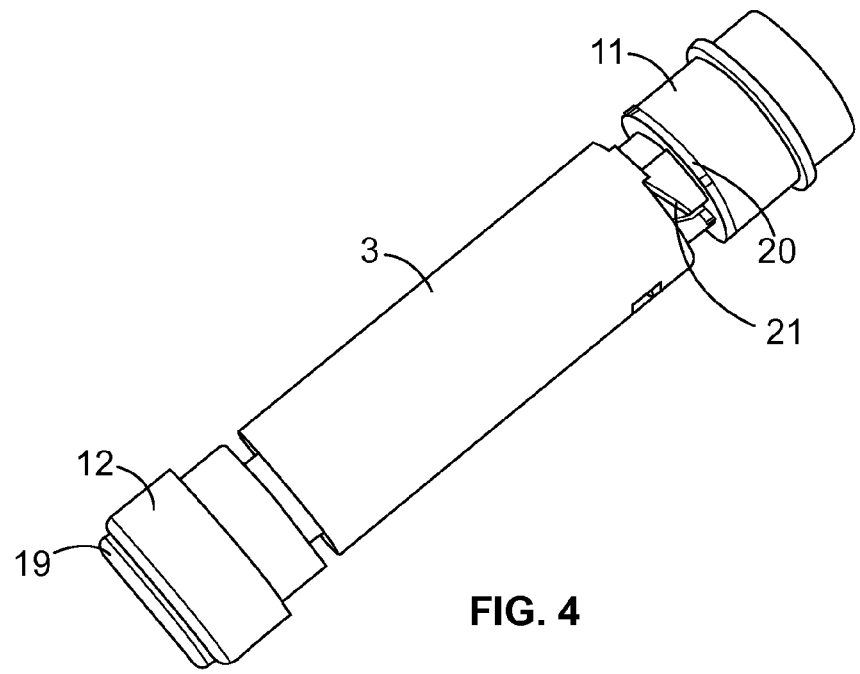
FIG. 4 is a perspective view of another embodiment of a dose setting mechanism in accordance with my invention for a drug delivery device such as the one shown in FIG. 1.
Figure 5:
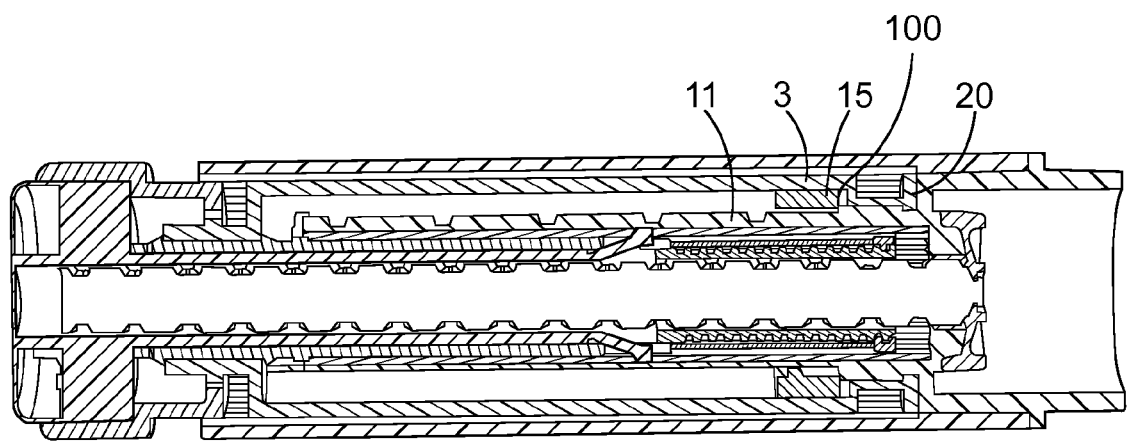
FIG. 5 illustrates a cut-away side view of the dose setting mechanism of FIG. 4.

FIGS. 4 and 5 illustrate yet another embodiment of my forced priming feature for an injection device similar to the type shown in FIG. 1. In this embodiment the forced priming feature contains a threaded collar 20, which cannot move axially relative to the inner body 11 and is also threadedly engaged with the number sleeve 3. To prime the injection device the user causes the threaded collar to rotate by either rotating the threaded collar or the cartridge holder 6 relative to body 17. Because the threaded collar 20 is initially threadedly engaged by threads 21 with the number sleeve, rotation of the threaded collar pulls the number sleeve forward (distal direction) via the thread engagement. During the final portion of rotation of the threaded collar the thread disengages from the number sleeve so that during dose setting the number sleeve is dialed normally without interference from the threaded collar 20.

As with the embodiment shown in FIGS. 2 and 3, this embodiment may contain stops to prevent a user from dialing out (setting a dose) prior to priming the device. A preferred design is to have the inner body contain a rotational counter stop that engages a stop on the number sleeve to prevent rotation. Movement of the number sleeve from the first non-primed position to the second primed position causes the spindle to move axially preloading the bung and thus priming the injection device. Likewise, the dose dial sleeve and the nut may have locking elements that engage when the threaded collar causes the dose dial sleeve to move axially during the priming operation.

In a preferred design, the movement of the dose dial sleeve along the rotational threaded collar may also cause the driver to rotate. This rotation of the driver may cause the spindle to advance towards the cartridge in the cartridge housing. This advancement of the spindle removes any potential initial separation between the spindle and the cartridge bung. In other words, this advancement of the spindle caused by the rotation of the dose dial sleeve and driver primes the drug delivery device.

As the dose setting mechanisms of my invention force a user to prime the device, the dose setting mechanisms described do not suffer from the drawback of possibly dispensing an incorrect dose due to the initial separation between the spindle and the cartridge bung. If a user attaches a needle to the drug delivery device before the user primes the device, then a small amount of drug may be expelled during the priming operation. Alternatively, if the user attaches the needle after priming the device or after setting the first dose, then the drug, which will be pressurized from the priming, will be expelled as the needle is connected to the drug delivery device. Accordingly, the drug amount resulting from the priming operation will be expelled before the needle is inserted into a user's skin.

In an exemplary arrangement, the drug delivery device may be designed to indicate to a user whether the device needs to be primed or does not need to be primed before dialing a dose. For instance, dose dial sleeve 3 may comprise a graphic printed on it that is displayed in the dose window 14 before the pen is primed. The graphic may display a character such as "P" or a phrase such as "Priming Needed." Other graphics are possible as well. Once a device has been primed, the graphic will no longer be displayed in the dose window.

Further, since the forced priming features of my invention contain irreversible locks or other non-return elements, the user does not have to prime the device prior to each subsequent dose. Accordingly, a dose setting mechanism in accordance with an exemplary embodiment forces a user to prime the device before the first dose is dialed, but does not force the user to prime the device for subsequent doses. However, in the event that the drug delivery device is reusable, it should be understood that a dose setting mechanism in accordance with an exemplary embodiment is designed so that the dose setting mechanism forces a user to prime the device each time a cartridge is replaced. In such a reusable device, the device is preferably designed so that a user could overcome the non-return elements. This may be accomplished, for example, by rotating the dose dial sleeve over a detent in the dialed position or possibly by pushing or pulling the dial sleeve in the proximal direction to disengage the lock. Other ways for overcoming the non-return elements are possible as well. Further, in this exemplary embodiment, it may be advantageous to force the user to do this before being able to remove the cartridge holder.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A dose setting mechanism for a drug delivery device comprising:
   a dial sleeve;
   a nut; and
   an inner body,
   wherein the dial sleeve is coupled to the nut that is threadedly engaged to the inner body, where the dial sleeve and nut are coupled to prevent relative rotational movement between the dose dial sleeve and the nut while allowing relative axial movement during priming,
   wherein the dial sleeve moves axially relative to the nut during priming of the drug delivery device from a first axial position to a second axial position where the dial sleeve irreversibly engages the nut, and
   wherein the dial sleeve translates along a helical path during dose setting of the drug delivery device.

2. A drug delivery device having a forced priming feature comprising
   a) a cartridge holder configured to contain a cartridge of medicament sealed with a bung;
   b) a dose dialing assembly containing a spindle configured to move the bung in an axial direction during dose delivery, an inner body with a rotational counter stop, a nut threadedly engaged with the inner body and rotationally fixed to a number sleeve having a proximal and a distal end, wherein the number sleeve has a first and a second axial position relative to the nut;

c) a sliding lock on the number sleeve that engages the nut when the number sleeve is in the second axial position; and d) a stop on the number sleeve that abuts the rotational counter stop on the inner body when the number sleeve is in the first axial position to prevent a user from setting a dose of medicament.

3. The drug delivery device of claim 2 wherein the sliding lock is irreversibly connected to the nut when the number sleeve is in the second axial position.

4. The drug delivery device of claim 2 wherein the sliding lock is prevented from engaging the nut when the number sleeve is in the first axial position by a frictional snap fit.

5. The drug delivery device of claim 2 where the spindle does not exert a force on the bung when the number sleeve is in the first axial position.

6. The drug delivery device of claim 2 where the spindle exerts a force on the bung when the number sleeve is in the second axial position.

7. A method of ensuring a user primes a drug delivery device before setting a first dose comprising, a) providing to a user a dose dial sleeve coupled with a nut threadedly engage on an inner body of a drug delivery device, where the dose dial and nut are coupled to prevent relative rotational movement between the dose dial sleeve and the nut while allowing relative axial movement during priming; and b) requiring the user to move the dose dial sleeve axially in the distal direction a specific distance to irreversibly engage the dial sleeve to the nut and causing a spindle to move axially to pre-load a bung in a container of medicament.

8. A method of ensuring a user primes a drug delivery device before setting a first dose comprising a) providing a user with a drug delivery device having a cartridge holder portion and a dose dialing portion containing a spindle, where the cartridge holder contains a cartridge containing a bung and medicament and where a number sleeve is in a first axial position;

b) preventing the user from dialing a dose through rotation of the number sleeve by providing a rotational stop on the number sleeve such that it engages a counter stop on an inner body when the number sleeve is in a first axial position, where engagement of the rotational stop and the counter stop prevents dialing of a dose through rotation of the number sleeve; and c) requiring the user to move the number sleeve from the first axial position to a second axial position to disengage the stop and counter stop and to engage a sliding lock on the number sleeve with a nut attached to the inner body.

9. A drug delivery device having a forced priming feature comprising a) a cartridge holder containing a cartridge of medicament sealed with a bung;

b) a dose dialing assembly containing a spindle configured to move the bung in an axial direction during dose delivery, an inner body with a rotational counter stop, a nut threadedly engaged with the inner body and attached to a number sleeve having a rotational stop and a proximal and a distal end, wherein the number sleeve has a first and a second axial position;

c) a collar threadedly engaged with the distal end of the number sleeve such that rotational of the collar causes the number sleeve to move from the first axial position where a user is prevented from setting a dose to the second axial position where a dose can then be set and where the rotational stop and counter stop are disengaged.

10. The drug delivery device of claim 9 where the collar is not threadedly engaged with the number sleeve when the number sleeve reaches the second axial position.

11. The drug delivery device of claim 9 where the spindle does not exert a force on the bung when the number sleeve is in the first axial position.

12. The drug delivery device of claim 9 where the spindle exerts a force on the bung when the number sleeve is in the second axial position.

13. A method of ensuring a user primes a drug delivery device before setting a first dose comprising a) providing a user with a drug delivery device having a cartridge holder portion and a dose dialing portion containing a spindle, where the cartridge holder contains a cartridge containing a bung and medicament and where a number sleeve is in a first axial position;

b) preventing the user from dialing a dose by providing a rotational stop on the number sleeve such that it engages a counter stop on an inner body when the number sleeve is in a first axial position; and c) requiring the user to rotate a collar threadedly engaged with the number sleeve to move the number sleeve from the first axial position to a second axial position where the stop and counter stop are disengaged.

14. The method of claim 13 where the collar and number sleeve become disengaged when the number sleeve reaches the second axial position.

\* \* \* \* \*